(12) United States Patent
Matsuda et al.

(10) Patent No.: US 10,022,166 B2
(45) Date of Patent: Jul. 17, 2018

(54) METHOD AND APPARATUSES FOR ANGULAR AND ROTATIONAL CORRECTION OF THE FEMUR

(71) Applicants: Biomet Manufacturing, LLC, Warsaw, IN (US); Biomet Sports Medicine, LLC, Warsaw, IN (US)

(72) Inventors: Dean Matsuda, Los Angeles, CA (US); Joseph M O'Reilly, Granger, IN (US)

(73) Assignees: Biomet Sports Medicine, LLC, Warsaw, IN (US); Biomet Manufacturing, LLC, Warsaw, IN (US)

( * ) Notice: Subject to any disclaimer, the term of this patent is extended or adjusted under 35 U.S.C. 154(b) by 37 days.

(21) Appl. No.: 14/989,367

(22) Filed: Jan. 6, 2016

(65) Prior Publication Data
US 2016/0199108 A1 Jul. 14, 2016

Related U.S. Application Data

(60) Provisional application No. 62/101,698, filed on Jan. 9, 2015.

(51) Int. Cl.
*A61B 17/72* (2006.01)
*A61B 17/84* (2006.01)
(Continued)

(52) U.S. Cl.
CPC .......... *A61B 17/72* (2013.01); *A61B 17/1717* (2013.01); *A61B 17/1725* (2013.01);
(Continued)

(58) Field of Classification Search
CPC . A61B 17/72; A61B 17/7233; A61B 17/7241; A61B 17/7283; A61B 17/1725
See application file for complete search history.

(56) References Cited

U.S. PATENT DOCUMENTS

| 4,169,470 A | 10/1979 | Ender |
| 2013/0325006 A1* | 12/2013 | Michelinie ......... A61B 17/7291 606/62 |

FOREIGN PATENT DOCUMENTS

| CN | 201551384 U | 8/2010 |
| WO | WO-2016112100 A1 | 7/2016 |

OTHER PUBLICATIONS

"International Application Serial No. PCT/US2016/012330, International Search Report dated Apr. 15, 2016", 6 pgs.
(Continued)

*Primary Examiner* — Julianna N Harvey
(74) *Attorney, Agent, or Firm* — Schwegman, Lundberg & Woessner, P.A.

(57) ABSTRACT

Methods, systems and apparatuses including an assembly for changing an orientation of a first portion of a femur relative to a second portion of the femur are disclosed. The assembly can include an intramedullary nail and a jig. The intramedullary nail can be insertable into an intramedullary canal of both the first portion of the femur and the second portion of the femur. The intramedullary nail can have a first section disposed between a proximal end and a distal end thereof. The first section can have at least one surface that is angled relative to an axis of the intramedullary nail. The jig can be coupled to and rotatable about the intramedullary nail to change a rotational position of the first portion of the femur relative to the second portion of the femur.

18 Claims, 9 Drawing Sheets

(51) Int. Cl.
*A61B 17/88* (2006.01)
*A61B 17/17* (2006.01)
(52) U.S. Cl.
CPC ...... *A61B 17/7208* (2013.01); *A61B 17/7216* (2013.01); *A61B 17/846* (2013.01); *A61B 17/8872* (2013.01); *A61B 17/8875* (2013.01)

(56) References Cited

OTHER PUBLICATIONS

"International Application Serial No. PCT/US2016/012330, Written Opinion dated Apr. 15, 2016", 7 pgs.
"European Application Serial No. 16704717.4, Communication Pursuant to Article 94(3) EPC dated May 15, 2018", 4 pgs.
"European Application Serial No. 16704717.4, Response dated Mar. 8, 2018 to Action dated Sep. 5, 2017", 15 pgs.

* cited by examiner

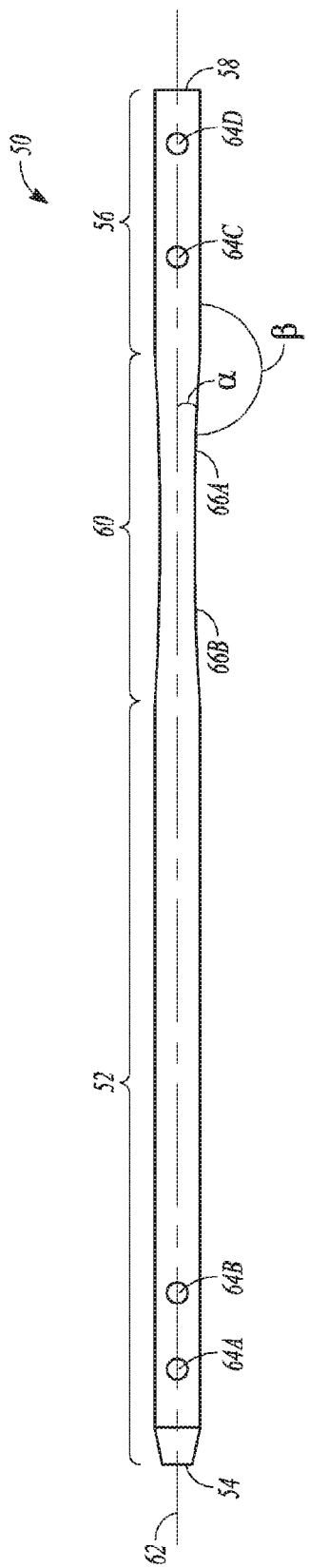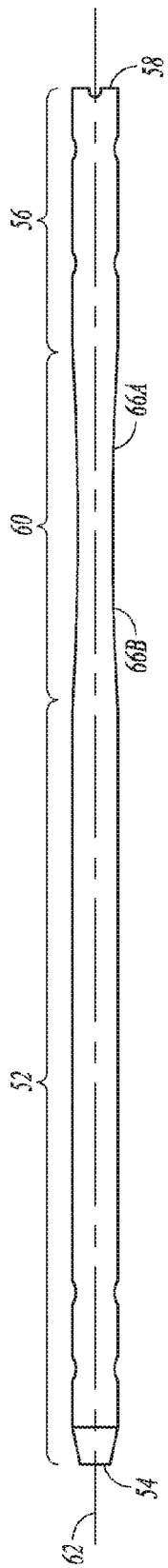
FIG. 3A
FIG. 3B

METHOD AND APPARATUSES FOR ANGULAR AND ROTATIONAL CORRECTION OF THE FEMUR

CLAIM OF PRIORITY

This application claims the benefit of U.S. Provisional Patent Application Ser. No. 62/101,698, filed on Jan. 9, 2015, the benefit of priority of which is claimed hereby, and which is incorporated by reference herein in its entirety.

FIELD

The present subject matter relates to surgical implants and methods, and more particularly, to apparatuses, systems and methods related to correcting a trauma or a deformity of the femur.

BACKGROUND

Surgical implants are utilized to treat a wide range of bodily injuries, maladies, and conditions. For example, orthopedic implants are used to replace or augment body components or portions of body components that cannot be regenerated or are no longer functioning properly. Orthopedic implants include spinal implants, dental implants, artificial shoulders, knees, hips, and ankle joints. Various trauma related implants can be utilized to help stabilize and treat a patient. Examples of trauma related implants include screws, nails, fixation systems, plate systems, etc.

Deformities of the femur can occur and can be treated with a femoral osteotomy. Indeed, in children, femoral osteotomy is a common operation to correct dysplasia and deformity of the femur from neuromuscular disease, developmental dysplasia of the hip, Perthes' disease, trauma and infection. Such maladies can result in varus deformation of the femoral neck among other deformities. Treatment of such maladies has typically been done with an open procedure that risks complications including infection, blood loss, and soft tissue damage. Additionally, traditional apparatuses used in such procedures are not sophisticated in design and have been responsible for surgical complications due to loosening from the bone of the femur.

OVERVIEW

The present inventors recognize, among other things, an opportunity for reducing surgical error, surgical complication, and patient discomfort in treating a trauma or deformity of the femur. More particularly, the present inventors have recognized that with traditional apparatuses for the treatment of a femur deformity, unnecessary surgical complications can occur, and that it can be difficult to accurately measure and determine the amount of deformity correction being achieved, In view of the foregoing, the present inventors have developed more sophisticated apparatuses and methods that can be used to achieve deformity correction without the need for a complex open procedure.

The apparatuses the inventors have developed can include a jig configured to adjust a rotational position of one portion of the femur relative to a second portion of the femur and an intramedullary nail that can be configured to allow for angular adjustment of the first portion of the femur relative to the second portion of the femur to achieve at least one of a desired varus-valgus, proximal-distal and anterior-posterior orientation of the first portion of the femur relative to the second portion of the femur. According to one example, the intramedullary can include a first section disposed between a proximal end and a distal end thereof. The first section can have at least one surface that is angled relative to an axis of the intramedullary nail. The adjustment of the first portion of the femur relative to the second portion to achieve at least one of the desired varus-valgus, proximal-distal and anterior-posterior orientation can include orienting the first portion of the femur relative to the at least one surface of the intramedullary nail.

To further illustrate the systems, apparatuses and methods disclosed herein, the following non-limiting examples are provided:

In Example 1, an assembly for changing an orientation of a first portion of a femur relative to a second portion of the femur are disclosed. The assembly can include an intramedullary nail and a jig. The intramedullary nail can be insertable into an intramedullary canal of bath the first portion of the femur and the second portion of the femur. The intramedullary nail can have a first section disposed between a proximal end and a distal end thereof. The first section can have at least one surface that is angled relative to an axis of the intramedullary nail. The jig can be coupled to and rotatable about the intramedullary nail to change a rotational position of the first portion of the femur relative to the second portion of the femur.

In Example 2, the apparatus of Example 1, wherein the at least one surface can be obliquely angled relative to an outer surface of the intramedullary nail and can be acutely angled relative to the axis of the intramedullary nail.

In Example 3, the apparatus of any one or any combination of Examples 1-2, wherein the first section can comprise a reduced diameter portion of the intramedullary nail and the first section has a generally hourglass shape.

Example 4, the apparatus of any one or any combination of Examples 1-3, wherein the at least one surface can be angled to allow for at least one of a desired varus-valgus, proximal-distal and anterior-posterior orientation of the first portion of the femur relative to the second portion of the femur.

In Example 5, the apparatus of any one or any combination of Examples 1-4, further comprising a fixation member that can be configured to be coupled to cortical bone of at least the first portion of the femur and can be configured to be coupled to the jig such that the rotation of the jig about the intramedullary nail changes a rotational position of the first portion of the femur relative to the second portion of the femur.

In Example 6, the apparatus of any one or any combination of Examples 1-5, wherein the jig can be positioned to have a portion thereof extend to generally proximal of the femur and the intramedullary nail can be configured for insertion into the intramedullary canal from generally proximal of the femur.

In Example 7, the apparatus of any one or any combination of Examples 1-6, wherein the intramedullary nail can be configured to be positioned to extend between the first portion of the femur and the second portion of the femur and the first section can be positioned at a gap between the first portion of the femur and the second portion of the femur.

In Example 8, the apparatus of any one or any combination of Examples 1-7, can further comprise one or more fasteners that can be configured to pass through the intramedullary nail and affix the intramedullary nail to the first portion of the femur.

In Example 9, a system for changing an orientation of a first portion of a femur relative to a second portion of the femur, the assembly can include an intramedullary nail, at least one screw, a jig and a fixation member. The intramedullary nail can be configured to be insertable into an intramedullary canal of both the first portion of the femur and the second portion of the femur. The intramedullary nail can have a first section disposed between a proximal end and a distal end thereof, the first section can have at least one surface that is angled relative to an axis of the intramedullary nail. The at least one screw can be configured to affix at least the first portion of the femur to the intramedullary nail. The jig can be configured to couple to and be rotatable about the intramedullary nail. The fixation member can be configured to couple to at least the first portion of the femur and the jig.

In Example 10, the system of Example 9, wherein the system can be configured such that rotation of the jig about the intramedullary nail changes a rotational position of the first portion of the femur relative to the second portion of the femur.

Example 11, the system of any one or any combination of Examples 9-10, wherein the at least one surface can be obliquely angled relative to an outer surface of the intramedullary nail and can be acutely angled relative to the axis of the intramedullary nail.

Example 12, the system of any one or any combination of Examples 9-11, wherein the first section can comprise a reduced diameter portion of the intramedullary nail and the first section can have a generally hourglass shape.

In Example 13, the system of any one or any combination of Examples 9-12, wherein the at least one surface can be angled to allow for at least one of a desired varus-valgus, proximal-distal and anterior-posterior orientation of the first portion of the femur relative to the second portion of the femur.

Example 14, an intramedullary nail can include a distal end section, a proximal end section, and an intermediate section. The intermediate section can be disposed between the distal end section and the proximal end section. The intermediate section can have a reduced diameter with respect to the proximal end section and the distal end section. The intermediate section can have at least one surface that forms an acute angle relative to an axis of the intramedullary nail.

In Example 15, the intramedullary nail of Example 14, wherein the at least one surface can be disposed at an oblique angle relative to an outer surface of the distal end section and the proximal end section of the intramedullary nail.

Example 16, a method of correcting a deformity of the femur, the method can include performing an osteotomy of the femur to divide the femur into at least a first portion and a second portion, disposing a jig adjacent the first portion of the femur, inserting a intramedullary nail into an intramedullary canal of both the first portion of the femur and the second portion of the femur, adjusting one or more of a varus-valgus, a proximal-distal and an anterior-posterior orientation of the first portion of the femur relative to the second portion of the femur, affixing the intramedullary nail to the first portion of the femur, affixing the jig to cortical bone of the first portion of the femur, and rotating the jig about the intramedullary nail to change a rotational position of the first portion of the femur relative to the second portion of the femur.

In Example 17, the method of Example 16, wherein the intramedullary nail can include a reduced diameter at an intermediate section disposed between a distal end section and a proximal end section, the intermediate section has at least one surface that forms an acute angle relative to an axis of the intramedullary nail.

In Example 18, the method of Example 17, wherein adjusting one or more of the varus-valgus, the proximal-distal and the anterior-posterior orientation of the first portion of the femur relative to the second portion of the femur can include orienting the first portion of the femur relative to the at least one surface of the intermediate section of the intramedullary nail.

In Example 19, the method of Example 17, wherein the intramedullary nail can be configured to be positioned to extend between the first portion of the femur and the second portion of the femur, and the first section can be positioned at a gap between the first portion of the femur and the second portion of the femur.

In Example 20, the method of Example 16, wherein affixing the intramedullary nail to the first portion of the femur can include passing a first anchor through the intramedullary nail and into the first portion of the femur, and wherein affixing the jig to the cortical bone of the first portion of the femur can include passing a second anchor into the cortical bone of the first portion of the femur and coupling the second anchor back to the jig.

Example 21, the systems, apparatuses or methods of any one or any combination of Examples 1-20 can optionally be configured such that all elements or options recited are available to use or select from.

These and other examples and features of the present apparatuses and methods will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

FIG. 3A is view of a side of the intramedullary nail of FIG. 3 according to an example of the present application.

FIG. 3B is a view of a second side of the intramedullary nail of FIG. 3 according to an example of the present application.

DETAILED DESCRIPTION

The present application relates to apparatuses that adjust an orientation of a first portion of a femur relative to a second portion of the femur and related systems and methods. The apparatuses can include a jig configured to adjust a rotational position of a first portion of the femur relative to a second portion of the femur and an intramedullary nail that can be configured to allow for angular adjustment of the first portion of the femur relative to the second portion of the femur to achieve at least one of a desired varus-valgus, proximal-distal and anterior-posted or orientation of the first portion of the femur relative to the second portion of the femur.

Figure 1:
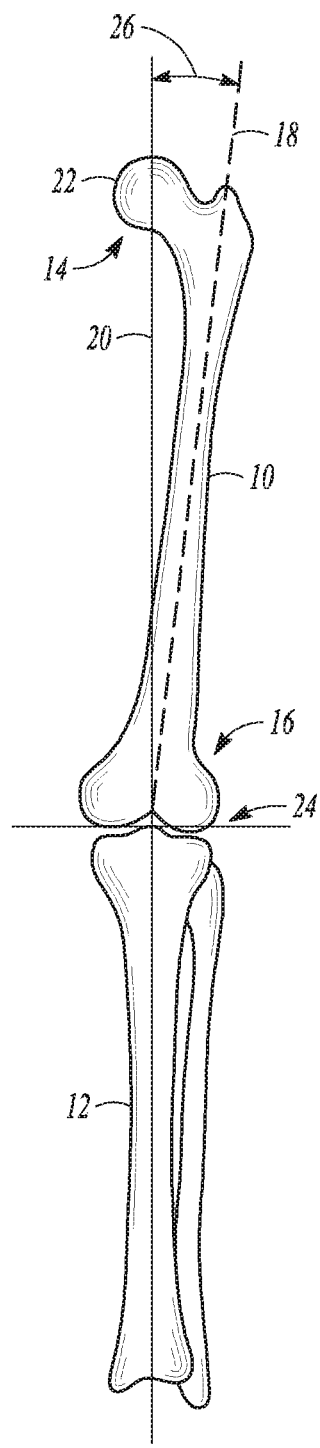
FIG. 1 is a schematic depiction of a health knee joint having a neutral mechanical axis according to an example of the present application.

FIG. 1 illustrates a front view of a natural femur 10 and a natural tibia 12. The femur 10 can include a proximal portion 14 and a distal portion 16. In FIG. 1, lower limb axes are also illustrated. The femur 10 has an anatomic axis 18 that coincides generally with its intramedullary canal. The femur 10 also has a mechanical axis 20, or load axis, running from the center of a femoral head to the center of a knee joint 24. The angle 26 extending between these two axes 18 and 20 varies among the patient population, but is generally on the order of between 5-7 degrees, inclusive.

Figure 2:
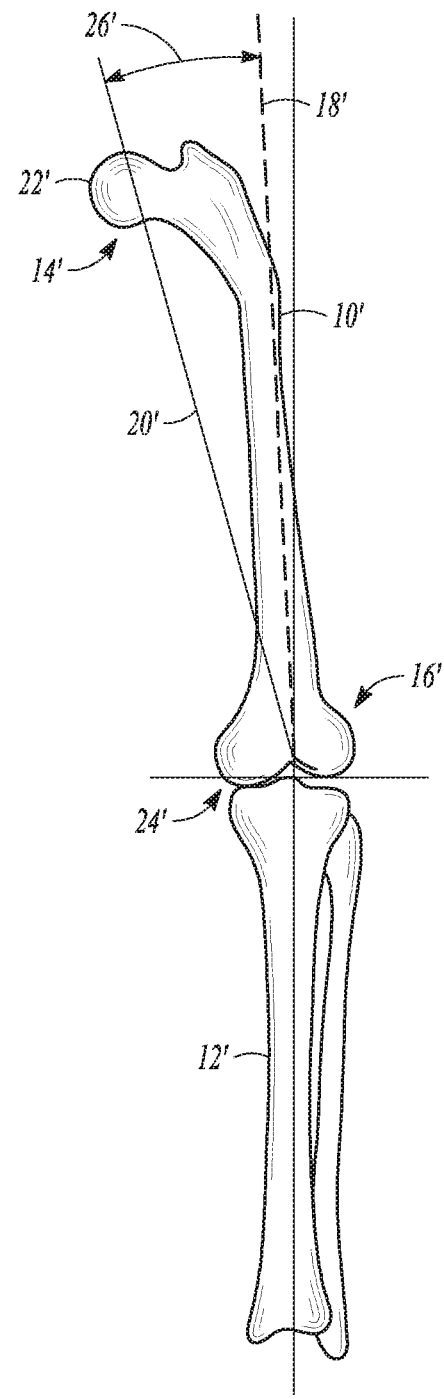
FIG. 2 is a schematic depiction of a knee joint having a deformity of the femur according to an example of the present application.

FIG. 2 illustrates a front view of femur 10' and tibia 12' with the femur 10' having a deformity. The femur 10' can include a proximal portion 14' and a distal portion 16'. As illustrated in FIG. 2, an anatomic axis 18' of the femur 10' may change between the proximal portion 14' and distal portion 16' due to the deformity. As a result of the deformity, a mechanical axis 20' of the femur 10' running from the center of a femoral head 22' to the center of a knee joint 24' can differ in orientation from that of the mechanical axis 20 of femur 10. For example, angle 26' between these two axes 18' and 20' can differ in degree from angle 26 of FIG. 1.

Figure 3:
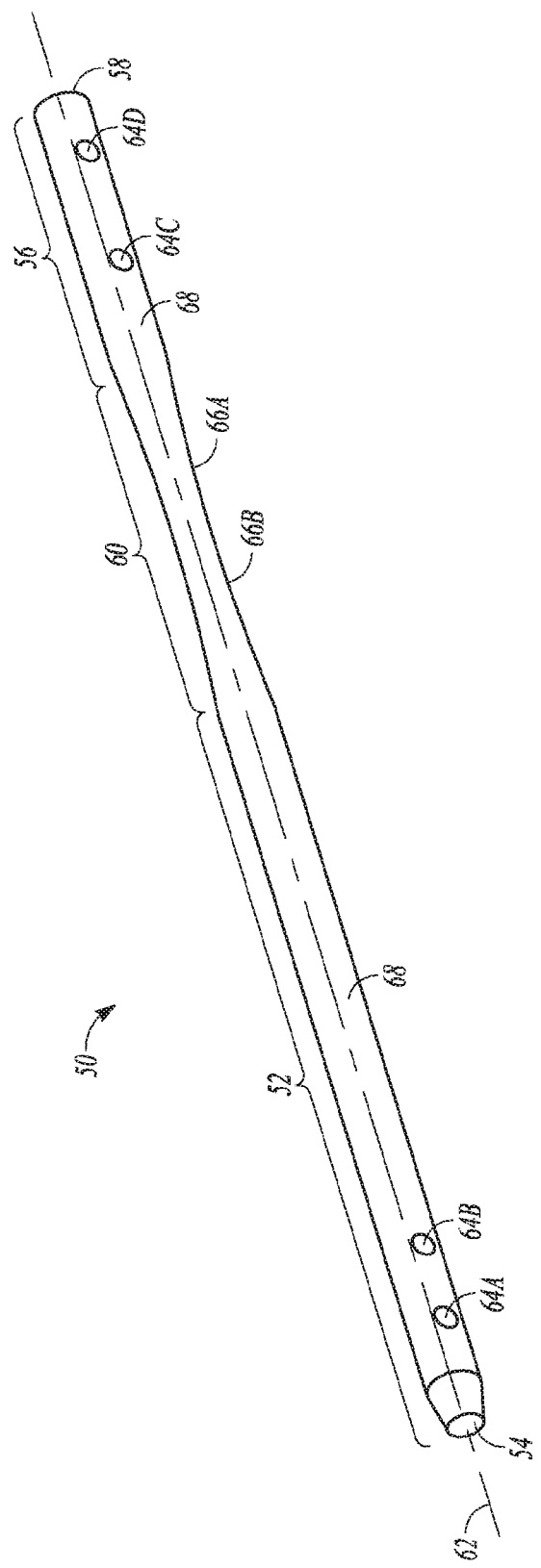
FIG. 3 is a perspective view of an intramedullary nail according to an example of the present application.

FIGS. 3 to 3B show an intramedullary nail 50 according to one example. The intramedullary nail 50 can include a distal end portion 52, a distal end 54, a proximal end portion 56, a proximal end 58, an intermediate portion 60, an axis 62, and bores 64A, 64B, 64C and 64D. As shown in FIGS. 3 to 3B, the intermediate portion 60 can include a first surface 66A and a second surface 66B. As shown in FIG. 3, the distal end portion 52 and the proximal end portion 56 can include an outer surface 68.

As shown in the example FIGS. 3 to 3B, the intermediate portion 60 can comprise a section of the intramedullary nail 50 disposed between the proximal end 58 and a distal end 54. More particularly, intermediate portion 60 can be disposed between and provide a transition between the distal end portion 52 and the proximal end portion 56. In the example of FIGS. 3 to 3B, the distal end portion 52 and the proximal end portion 56 can be cylindrical in shape (e.g., can have a circular cross-section with similar diameters for each respective portion). The bores 64A, 64B, 64C and 64D can comprise thru bores that pass through the distal end portion 52 and the proximal end portion 56. The distal end portion 52, the proximal end portion 56 and the intermediate portion 60 can be aligned along the axis 62. According to the example of FIGS. 3 to 3B where the distal end portion 52 and the proximal end portion 56 can be cylindrical in shape, the axis 62 can comprise an axis of symmetry for each portion.

In the example of FIGS. 3 to 3B, the proximal end 58 can be configured to couple with a device such as the jig (discussed subsequently). The distal end 54 can be tapered for insertion into an intramedullary canal of a patient as illustrated subsequently. The bores 64A, 64B, 64C and 64D can vary in number and in orientation as desired. In FIGS. 3 to 3B, the bores 64A, 64B, 64C and 64D are oriented so that they can extend generally medial-lateral through the intramedullary nail 50 when intraoperatively positioned. However, in other examples, the bores 64A, 64B, 64C and 64D may extend one or more of medial-lateral, proximal-distal, and anterior-posterior through the intramedullary nail 50.

The first surface 66A and the second surface 66B of the intermediate portion 60 can be angled relative to the axis 62 of the intramedullary nail 52 as shown in FIG. 3B. More particularly, the first surface 66A and/or the second surface 66B can be obliquely angled (only the oblique angle β between the first surface 66A is indicated in FIG. 3B) relative to the outer surface 68 of the distal end portion 52 and the proximal end portion 56. Similarly, the first surface 66A and the second surface 66B can be acutely angled (only the acute angle α between the first surface 66A is indicated in FIG. 3B) relative to the axis 62 of the intramedullary nail 50.

According to the example of FIGS. 3 to 3B where the intramedullary nail is generally cylindrical in shape, the intermediate section 60 can comprise a reduced diameter portion of the intramedullary nail 50 (i.e. can have a reduced diameter with respect to one or both of the diameters of the distal end portion 52 and the proximal end portion 56), and the intermediate portion 60 can have a generally hourglass shape. According to other examples, the first surface 66A and/or second surface 66B may not extend entirely around the entire circumference of the intermediate portion 60 but instead can be disposed along particular portions of the circumference as desired. Although shown as having a similar angulation in FIGS. 3 to 3B, the angle of the first surface 66A and the second surface 66B can differ from one another as desired. As will be illustrated in further Figures subsequently, the first surface 66A and the second surface 66B can be angled to allow for at least one of a desired varus-valgus, proximal-distal and anterior-posterior orientation of a first portion of the femur relative to a second portion of the femur (e.g., to allow for the first portion of the femur to be angled varus-valgus, proximal-distal and anterior-posterior relative to the second portion of the femur).

Figure 4A:
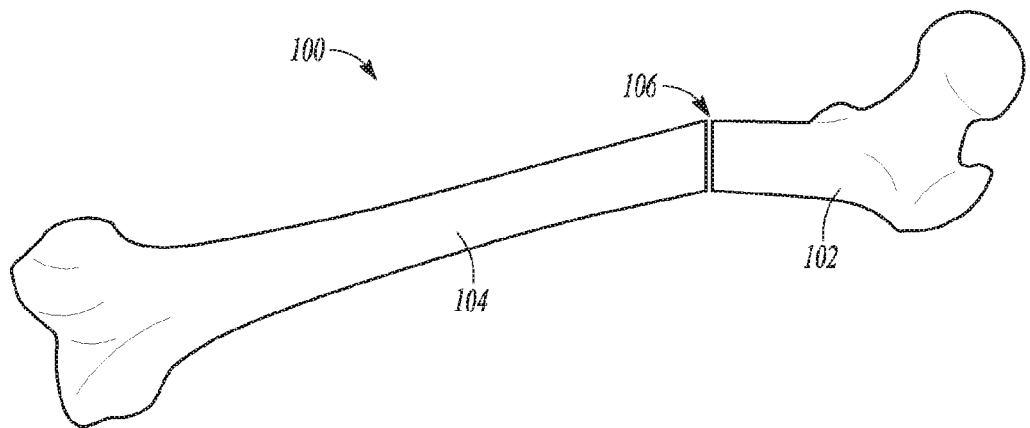
FIG. 4A is a schematic view of femur following an osteotomy that divides the femur into a first section and a second section according to an example of the present application.
Figure 4B:
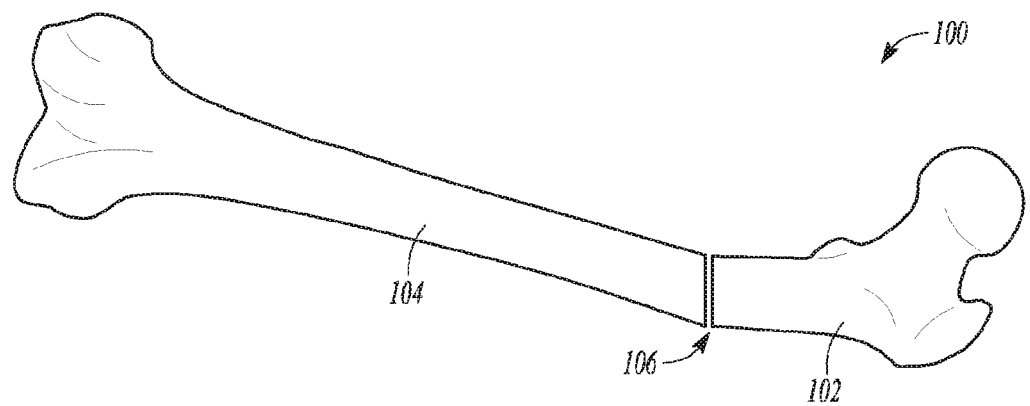
FIG. 4B is a second schematic view of the femur of FIG. 4A from a different perspective according to an example of the present application.

FIGS. 4A and 4B show an example of a femur 100 having a deformity. An osteotomy can be performed on the femur 100 to separate the femur 100 into a first portion 102 and a second portion 104. The osteotomy can create a gap 106 been the first portion 102 and the second portion 104. The osteotomy can be performed to create the gap 106 at an area where the first portion 102 changes orientation and is oriented at a different angle relative to the knee joint than the second portion 104, for example.

In some examples, the osteotomy can be performed using conventional osteotome tools (e.g., a chisel). In other examples, an intramedullary bone saw such as the commercially available intramedullary bone saw from Zimmer Biomet Inc. of Warsaw, Ind. can be used to perform the osteotomy from within the intramedullary canal outward.

Figure 5:
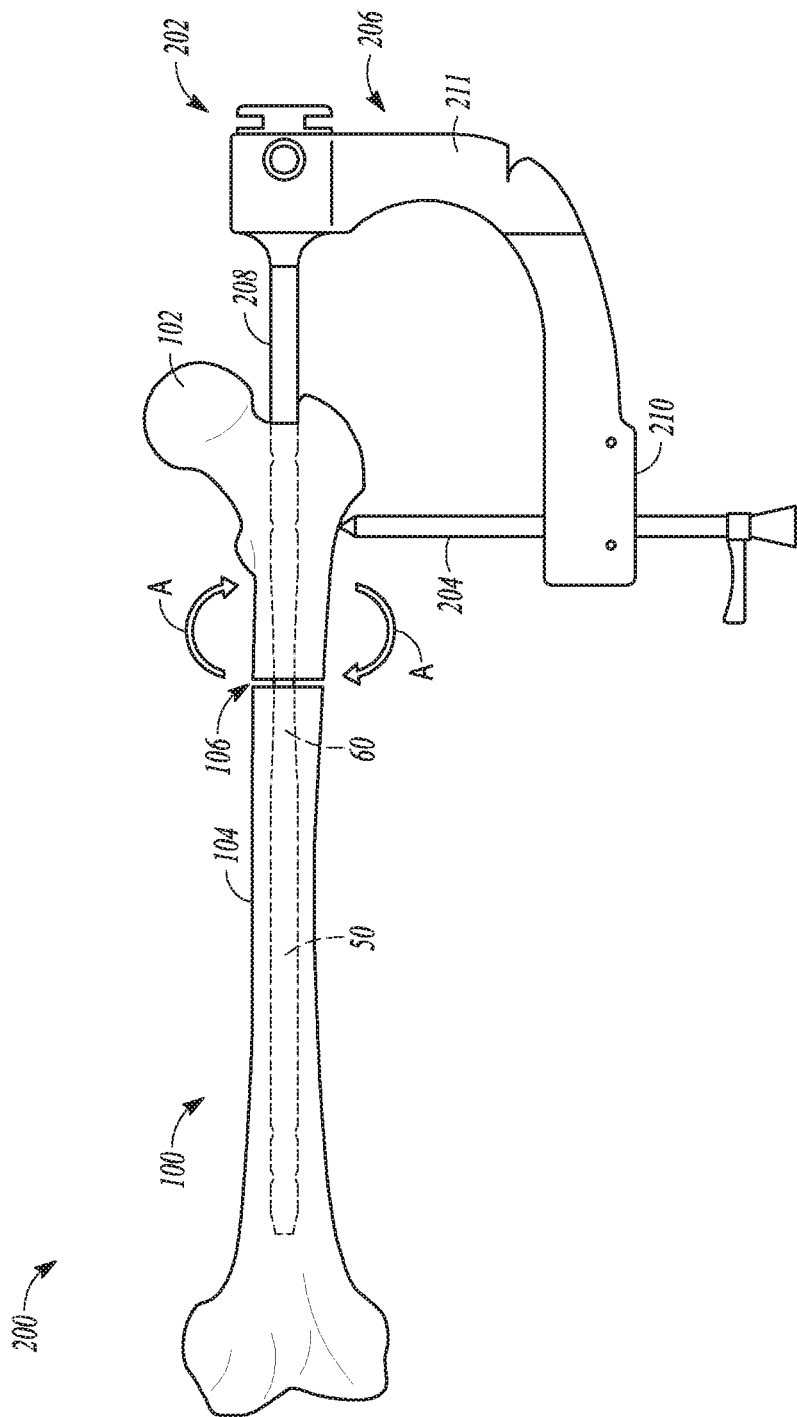
FIG. 5 is a view of an assembly comprising a jig, an fixation device, and the intramedullary nail of FIGS. 3-3B with the intramedullary nail inserted into the femur of FIGS. 4A and 4B according to an example of the present application.

FIG. 5 shows an assembly 200 used to change an orientation of the first portion 102 of the femur 100 relative to the second portion 104 of the femur 100. The assembly 200 includes the intramedullary nail 50 (previously described), a jig 202, and a fixation device 204. The jig 202 can include a body 206 and an insertion member 208.

In the example of FIG. 5, the jig 202 can be positioned to have a portion thereof extend to generally proximal of the femur 100 and the intramedullary nail 50 can be configured for insertion into the intramedullary canal from generally proximal of the femur 100. However, in other examples the jig 202 can be positioned to have a portion thereof extend to generally distal of the femur 100 (e.g. to adjacent the knee joint) and the intramedullary nail 50 can be configured for insertion into the intramedullary canal from generally distal of the femur 100.

The jig 202 can couple to the fixation device 204 and can be coupled to and rotatable about the intramedullary nail 50 as further described and illustrated herein. More particularly, the body 206 of the jig 202 can contain one or more apertures along a distal portion 210. The one or more apertures can be configured to receive the fixation device 204. In some examples, the distal portion 210 can be moveable (e.g., extendable/contractible and/or rotatable) relative to a proximal portion 211 of the body 206. The body 206 can be shaped to extend around the femur 100 from a side thereof to one of proximal or distal thereto. The insertion member 208 can be received in a second aperture of the body 206 can be configured to extend into the intramedullary canal of the femur 100 to couple with the intramedullary nail 50. The body 206 can be rotatable relative to the insertion member 208.

The intramedullary nail 50 can be insertable into the intramedullary canal of both the first portion 102 of the femur 100 and the second portion 104 of the femur 100 as shown in FIG. 5. As shown in FIG. 5, the intramedullary nail 50 can be configured to be positioned to extend between the first portion 102 of the femur 100 and the second portion 104 of the femur 100 and the intermediate section 60 can be positioned at the gap 106 between the first portion 102 and the second portion 104. The positioning of the intramedullary nail 50 with the intermediate section 60 at the gap 106 and/or the angulation of the first surface 66A and/or second surface 66B (FIG. 3B) can allow for adjustment of the first portion 102 relative to the second portion 104 (as shown by arrows A) to achieve at least one of the desired varus-valgus, proximal-distal and anterior-posterior orientation of the first portion 102 relative to the second portion 104.

Figure 6:
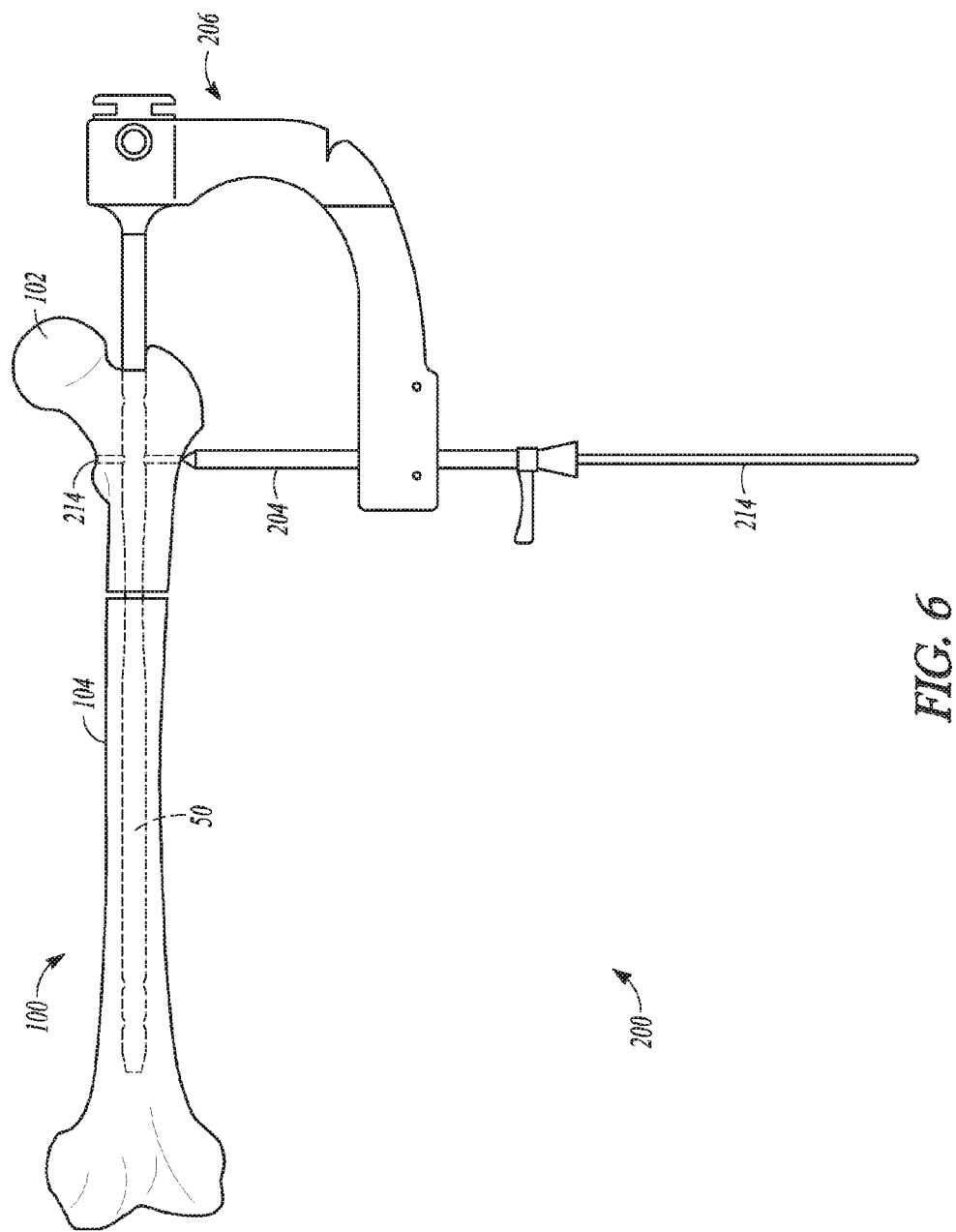
FIG. 6 is a view of the assembly of FIG. 5 and further illustrating a drill being passed through the fixation device and into the first portion of the femur and through the intramedullary nail according to an example of the present application.

As shown in FIG. 6, once the desired varus-valgus, proximal-distal and anterior-posterior orientation of the first portion 102 relative to the second portion 104 is achieved, the fixation device 204 can be inserted through the body 206 and the body 206 and/or fixation device 204 can be oriented relative to the first portion 102 and the intramedullary nail 50 to allow a drill 214 to be passed into the first portion 102 to drill the femur 100. The drill 214 can be oriented to align with and pass through one of the bores 64A, 64B, 64C and 64D (FIGS. 3 to 3B) of the intramedullary nail 50.

Figure 7:
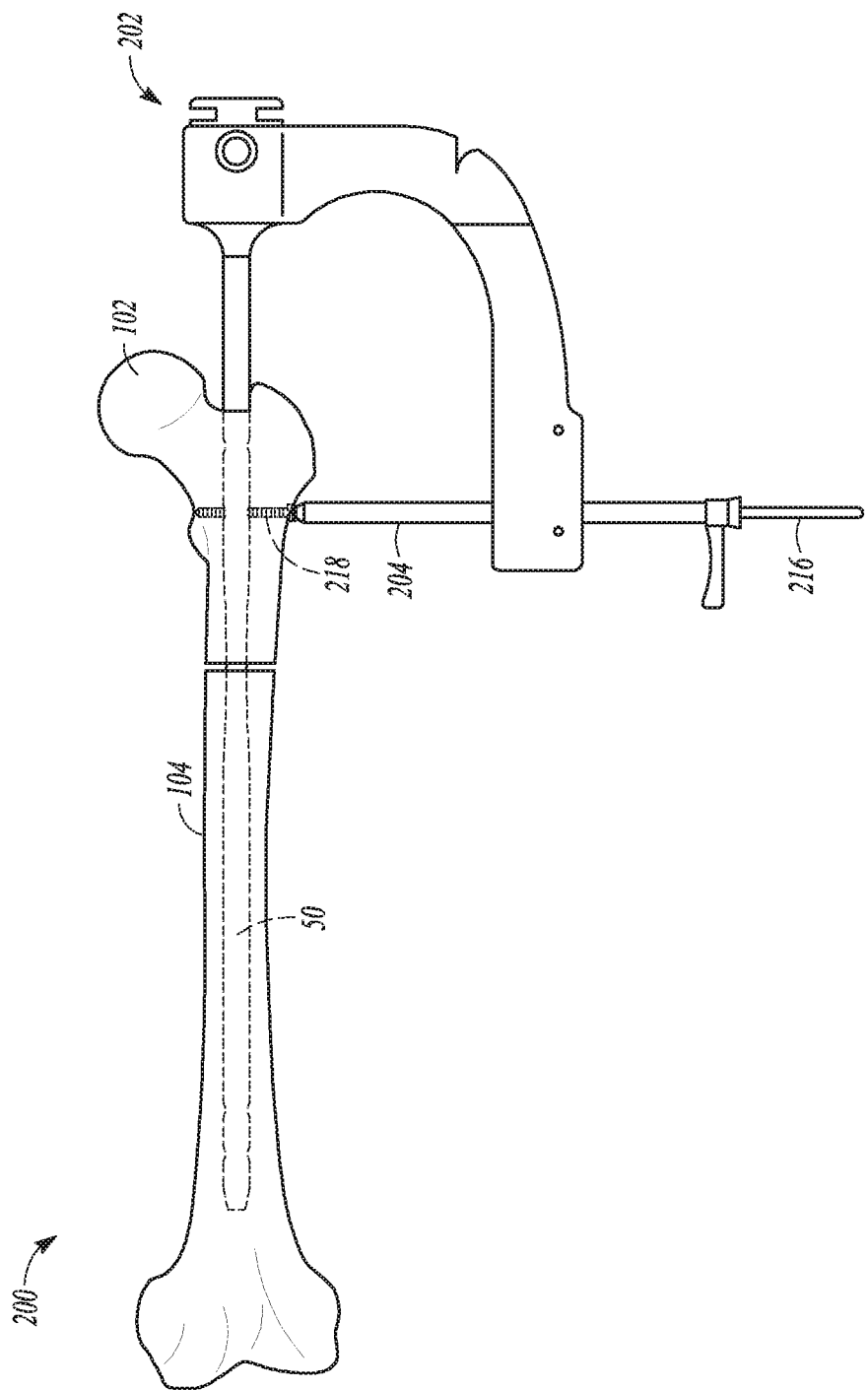
FIG. 7 is a view of the assembly of FIG. 5 and further illustrating a first fastener affixing the intramedullary nail to the first portion of the femur according to an example of the present application.

Once an aperture is created in the first portion 102 by the drill 214, the fixation device 204 and jig 202 can be configured to be used in combination with a second tool 216 to advance a first fastener 218 (also referred to as a first anchor) into the aperture as shown in FIG. 7. The first fastener 218 (e.g., a bone screw or the like) can pass into the first portion 102 and through the intramedullary nail 50, and thus, can affix the intramedullary nail 50 to the first portion 102. This configuration can allow the first portion 102 to be maintained at the desired varus-valgus, proximal-distal and anterior-posterior relative to the second portion 104 for a remainder of the procedure. Thus, the first portion 102 and the intramedullary nail 50 can be coupled together such that the first portion 102 and the intramedullary nail 50 are rotatable together but the angular orientation in one or more of varus-valgus, proximal-distal and anterior-posterior of the first portion 102 relative to the second portion 104 can be maintained by the first fastener 18 affixing the intramedullary nail 50 to the first portion 102.

Figure 8:
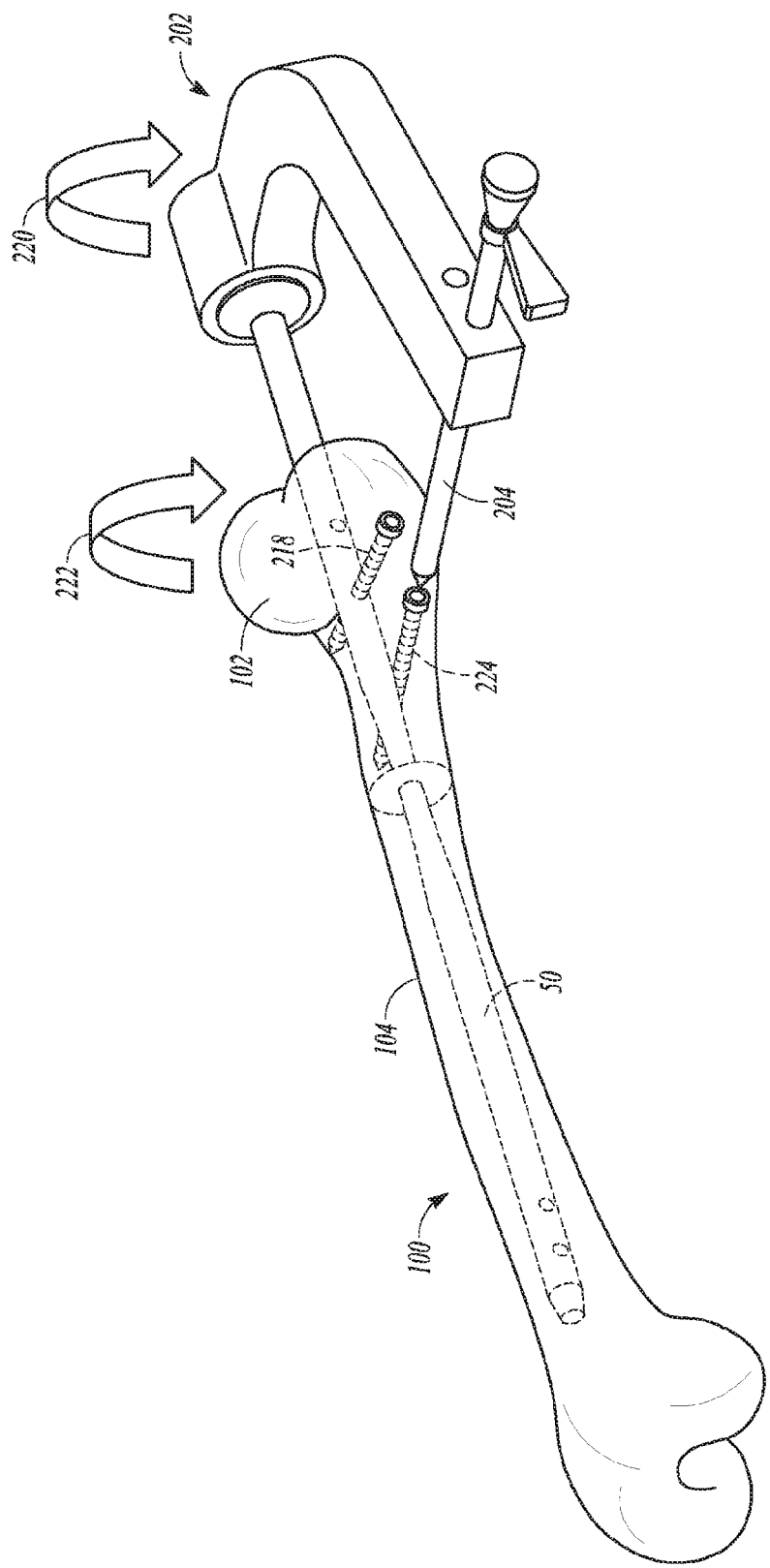
FIG. 8 is a perspective view of the assembly of FIG. 7 and further illustrating a second fastener affixing the jig to cortical bone of the first portion of the femur and further illustrating rotation of the jig about the intramedullary nail to change a rotational position of the first portion of the femur relative to the second portion of the femur according to an example of the present application.

FIG. 8 shows and example where the jig 202 can be coupled to and rotatable about the intramedullary nail 50 to change a rotational position of the first portion 102 of the femur 100 relative to the second portion 104 as shown by arrows 220 and 222.

In the example of FIG. 8, the jig 202 and the fixation device 204 can be been reoriented from the position of FIG. 7 to a second position such as the one shown, and a second fastener 224 can be advanced into cortical bone of the first portion 102. This second fastener 224 can couple the jig 202 to the first portion 102 via the fixation device 204. With the intramedullary nail 50 affixed to the first portion 102 and the jig 202 affixed to the first portion 102 via the fixation member 204, the jig 202 can be rotated about the intramedullary nail 50 to rotate the first portion 102 relative to the second portion 104. In this manner, the rotational position of the first portion 102 of the femur 100 relative to the second portion 104 of the femur 100 can be adjusted as desired.

Figure 9A:
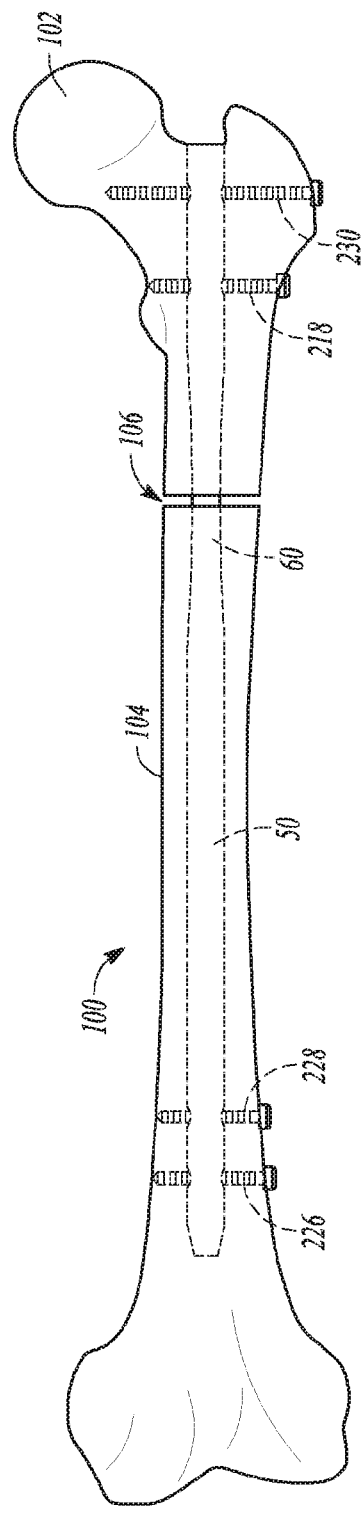
FIGS. 9A and 9B show the intramedullary nail affixed to the first portion and the second portion of the femur and the first portion of the femur oriented at a desired position relative to the second portion of the femur according to an example of the present application.
Figure 9B:
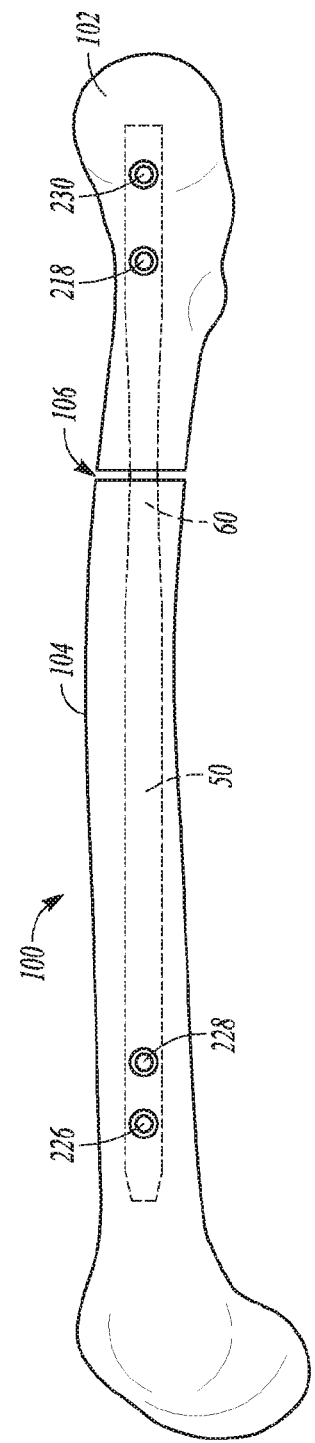

FIGS. 9A and 9B show an example of the femur 100 after desired rotational alignment and/or desired varus-valgus, proximal-distal and anterior-posterior angular positioning of the first portion 102 relative to the second portion 104 has been performed. As discussed previously, the intramedullary nail 50 is configured to be positioned to extend between the first portion 102 of the femur 100 and the second portion 104 and the intermediate portion 60 is positioned at the gap 106 between the first portion 102 and the second portion 104. As shown in FIGS. 9A and 9B, once desired orientation of the first portion 102 relative to the second portion 104 is achieved, additional fasteners 226, 228, and 230 (in addition to first fastener 218) can be inserted into the first and/or second portion and through apertures in the intramedullary nail 50 further affixing the intramedullary nail 50 to the femur 100. The second fastener 224 (FIG. 8) can be removed.

According to an exemplary method of present disclosure a deformity correction of a femur is disclosed. The method can include performing an osteotomy of the femur to divide the femur into at least a first portion and a second portion, disposing a jig adjacent the first portion of the femur, inserting a intramedullary nail into an intramedullary canal of both the first portion of the femur and the second portion of the femur, adjusting one or more of a varus-valgus, a proximal-distal and an anterior-posterior orientation of the first portion of the femur relative to the second portion of the femur, affixing the intramedullary nail to the first portion of the femur, affixing the jig to cortical bone of the first portion of the femur, and rotating the jig about the intramedullary nail to change a rotational position of the first portion of the femur relative to the second portion of the femur.

According to further examples, the intramedullary nail can include a reduced diameter at an intermediate section disposed between a distal end section and a proximal end section. The intermediate section can have at least one surface that forms an acute angle relative to an axis of the intramedullary nail. The adjusting one or more of the varus-valgus, the proximal-distal and the anterior-posterior orientation of the first portion of the femur relative to the second portion of the femur can include orienting the first portion of the femur relative to the at least one surface of the intermediate section of the intramedullary nail. The intramedullary nail can be configured to be positioned to extend between the first portion of the femur and the second portion of the femur, and the first section can be positioned at a gap between the first portion of the femur and the second portion of the femur. The affixing the intramedullary nail to the first portion of the femur can include passing a first anchor through the intramedullary nail and into the first portion of the femur. The affixing of the jig to the cortical bone of the first portion of the femur can include passing a second anchor into the cortical bone of the first portion of the femur and coupling the second anchor back the jig.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more" In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein," Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. An apparatus for changing an orientation of a first portion of a femur relative to a second portion of the femur, the apparatus comprising:
    a single piece intramedullary nail insertable into an intramedullary canal of both the first portion of the femur and the second portion of the femur, the intramedullary nail having a first section disposed between a proximal end and a distal end thereof, the first section having at least one surface that is angled relative to a longitudinal axis of the intramedullary nail; and
    a jig coupled to and rotatable about the intramedullary nail to change a rotational position of the first portion of the femur relative to the second portion of the femur, wherein the proximal end, the distal end and the first section of the intramedullary nail all share the longitudinal axis in common both before the rotational position of the first portion of the femur is changed relative to the second portion of the femur and after the rotational position of the first portion of the femur is changed relative to the second portion of the femur to achieve a desired position.

2. The apparatus of claim 1, wherein the at least one surface is obliquely angled relative to an outer surface of the intramedullary nail and is acutely angled relative to the longitudinal axis of the intramedullary nail.

3. The apparatus of claim 1, wherein the first section comprises a reduced diameter portion of the intramedullary nail and the first section has a generally hourglass shape.

4. The apparatus of claim 1, wherein the at least one surface is angled to allow for at least one of a desired varus-valgus, proximal-distal and anterior-posterior orientation of the first portion of the femur relative to the second portion of the femur.

5. The apparatus of claim 1, further comprising a fixation member configured to be coupled to cortical bone of at least the first portion of the femur and configured to be coupled to the jig such that the rotation of the jig about the intramedullary nail changes a rotational position of the first portion of the femur relative to the second portion of the femur.

6. The apparatus of claim 1, wherein the jig is configured to have a portion thereof extend to generally proximal of the femur when positioned and the intramedullary nail is configured for insertion into the intramedullary canal from generally proximal of the femur.

7. The apparatus of claim 1, wherein the intramedullary nail is configured to be positioned to extend between the first portion of the femur and the second portion of the femur and the first section is configured to be positioned at a gap between the first portion of the femur and the second portion of the femur.

8. The apparatus of claim 1, further comprising one or more fasteners configured to pass through the intramedullary nail and affix the intramedullary nail to the first portion of the femur.

9. An apparatus for changing an orientation of a first portion of a femur relative to a second portion of the femur, the apparatus comprising:
   a single piece intramedullary nail insertable into an intramedullary canal of both the first portion of the femur and the second portion of the femur, the intramedullary nail having a first section disposed between a proximal end and a distal end thereof, the first section having at least one surface that is angled relative to a longitudinal axis of the intramedullary nail;
   one or more fasteners configured to pass through the intramedullary nail and affix the intramedullary nail to the first portion of the femur;
   a jig coupled to and rotatable about the intramedullary nail to change a rotational position of the first portion of the femur relative to the second portion of the femur, wherein the proximal end, the distal end and the first section of the intramedullary nail all share the longitudinal axis in common both before the rotational position of the first portion of the femur is changed relative to the second portion of the femur and after the rotational position of the first portion of the femur is changed relative to the second portion of the femur to achieve a desired position; and
   a fixation member configured for coupling at least the first portion of the femur and the jig.

10. The apparatus of claim 9, wherein the at least one surface is obliquely angled relative to an outer surface of the intramedullary nail and is acutely angled relative to the longitudinal axis of the intramedullary nail.

11. The apparatus of claim 9, wherein the first section comprises a reduced diameter portion of the intramedullary nail and the first section has a generally hourglass shape.

12. The apparatus of claim 9, wherein the at least one surface is angled to allow for at least one of a desired varus-valgus, proximal-distal and anterior-posterior orientation of the first portion of the femur relative to the second portion of the femur.

13. The apparatus of claim 9, wherein the first section of the intramedullary nail comprises an intermediate section disposed between a distal end section and a proximal end section, the intermediate section having a reduced diameter with respect to the proximal end section and the distal end section, wherein the intermediate section has the at least one surface that forms an acute angle relative to the longitudinal axis of the intramedullary nail.

14. The apparatus of claim 13, wherein the at least one surface is disposed at an oblique angle relative to an outer surface of the distal end section and the proximal end section of the intramedullary nail.

15. An apparatus for changing an orientation of a first portion of a femur relative to a second portion of the femur, the apparatus comprising:
   a single piece intramedullary nail insertable into an intramedullary canal of both the first portion of the femur and the second portion of the femur, the intramedullary nail comprising:
      a distal end section;
      a proximal end section; and
      an intermediate section disposed between the distal end section and the proximal end section, the intermediate section having a reduced diameter with respect to the proximal end section and the distal end section, wherein the intermediate section has at least one surface that forms an acute angle relative to a longitudinal axis of the intramedullary nail;
   one or more fasteners configured to pass through the intramedullary nail and affix the intramedullary nail to the first portion of the femur;
   a jig coupled to and rotatable about the intramedullary nail to change a rotational position of the first portion of the femur relative to the second portion of the femur, wherein the proximal end section, the distal end section and the intermediate section of the intramedullary nail all share the longitudinal axis in common both before the rotational position of the first portion of the femur is changed relative to the second portion of the femur and after the rotational position of the first portion of the femur is changed relative to the second portion of the femur to achieve a desired position; and
   a fixation member configured for coupling at least the first portion of the femur and the jig.

16. The apparatus of claim 15, wherein the at least one surface is disposed at an oblique angle relative to an outer surface of the distal end section and the proximal end section of the intramedullary nail.

17. The apparatus of claim 15, wherein the at least one surface is angled to allow for at least one of a desired varus-valgus, proximal-distal and anterior-posterior orientation of the first portion of the femur relative to the second portion of the femur.

18. The apparatus of claim 15, wherein the intramedullary nail is configured to be positioned to extend between the first portion of the femur and the second portion of the femur and the intermediate section is configured to be positioned at a gap between the first portion of the femur and the second portion of the femur.

* * * * *